(12) United States Patent
Fujii

(10) Patent No.: US 9,057,067 B2
(45) Date of Patent: Jun. 16, 2015

(54) METHOD FOR TRANSFECTING NUCLEIC ACID TO CELL AND NUCLEIC ACID COMPLEX

(75) Inventor: Masayuki Fujii, Fukuoka (JP)

(73) Assignee: Kinki University, Osaka (JP)

( * ) Notice: Subject to any disclaimer, the term of this patent is extended or adjusted under 35 U.S.C. 154(b) by 0 days.

(21) Appl. No.: 13/808,695

(22) PCT Filed: Jul. 7, 2011

(86) PCT No.: PCT/JP2011/065612
§ 371 (c)(1),
(2), (4) Date: Jan. 7, 2013

(87) PCT Pub. No.: WO2012/008361
PCT Pub. Date: Jan. 19, 2012

(65) Prior Publication Data
US 2013/0115700 A1    May 9, 2013

(30) Foreign Application Priority Data
Jul. 10, 2010 (JP) ................................ 2010-157367

(51) Int. Cl.
A61K 48/00 (2006.01)
C07K 4/00 (2006.01)
C12N 15/87 (2006.01)
C12N 15/113 (2010.01)
C12N 15/11 (2006.01)

(52) U.S. Cl.
CPC ............ *C12N 15/113* (2013.01); *C12N 15/111* (2013.01); *C12N 15/87* (2013.01); *C12N 2310/14* (2013.01); *C12N 2320/32* (2013.01); *C12Y 207/07049* (2013.01); *C12N 15/1137* (2013.01)

(58) Field of Classification Search
CPC .............. C12N 15/111; C12N 15/113; C12N 15/1137; C12N 15/87; C12N 2310/14; C12N 2320/32; C12Y 207/07049
USPC .................... 435/375, 455; 530/322
See application file for complete search history.

(56) References Cited

U.S. PATENT DOCUMENTS

| | | |
|---|---|---|
| 5,547,932 A | 8/1996 | Curiel et al. |
| 5,981,273 A | 11/1999 | Curiel et al. |
| 6,022,735 A | 2/2000 | Curiel et al. |
| 6,051,429 A * | 4/2000 | Hawley-Nelson et al. ... 435/458 |
| 6,077,663 A | 6/2000 | Curiel et al. |
| 6,274,322 B1 | 8/2001 | Curiel et al. |
| 2002/0055174 A1 | 5/2002 | Rittner et al. |
| 2003/0026840 A1 | 2/2003 | Plank et al. |
| 2003/0125242 A1 | 7/2003 | Rosenecker et al. |
| 2004/0132188 A1 | 7/2004 | Rittner et al. |
| 2008/0071068 A1 | 3/2008 | Oba et al. |
| 2009/0239939 A1 | 9/2009 | Plank et al. |
| 2009/0317906 A1 * | 12/2009 | Weber et al. .................. 435/354 |

FOREIGN PATENT DOCUMENTS

| | | |
|---|---|---|
| JP | 10-146191 | 6/1998 |
| JP | 10-506001 | 6/1998 |
| JP | 11-290073 | 10/1999 |
| JP | 2001-288200 | 10/2001 |
| JP | 2002-316997 | 10/2002 |
| JP | 2003-503370 | 1/2003 |
| JP | 2003-514564 | 4/2003 |
| JP | 2004-65238 | 3/2004 |
| JP | 2005-312397 | 11/2005 |

OTHER PUBLICATIONS

Kubo et al. Nucleic Acids Symposium Series No. 48 99-100.*
Laufer et al. Selected Strategies for the Delivery of siRNA In Vitro and In Vivo. V.A. Erdmann and J. Barciszewski (eds.), RNA Technologies and Their Applications, RNA Technologies, DOI 10.1007/978-3-642-12168-5_2, Springer-Verlag, Berlin, Heidelberg 2010.*
International Search Report issued Sep. 20, 2011 in International (PCT) Application No. PCT/JP2011/065612.
I. Diala et al., "Antisense Inhibition of Human Telomerase by Phosphorothioate Oligonucleotide-Peptide Conjugates", Nucleic Acids Symposium Series, No. 52, pp. 679-680, 2008.
S. Murao et al., "Organic Synthesis and Antisense Effects of Oligonucleotide-Peptide Conjugates", Current Organic Chemistry, vol. 13, No. 14, pp. 1366-1377, 2009.
S. Deshayes et al., "Delivery of Proteins and Nucleic Acids using a Non-Covalent Peptide-Based Strategy", Advanced Drug Delivery Reviews, vol. 60, No. 4-5, pp. 537-547, 2008.
A. Eguchi et al., "siRNA Delivery using Peptide Transduction Domains", Trends Pharmacol. Sci., vol. 30, No. 7, pp. 341-345, 2009.
Supplementary European Search Report dated Nov. 7, 2013 in European Application No. 11806691.9.
Legendre e al., "Cyclic Amphipathic Peptide-DNA Complexes Mediate High-Efficiency Transfection of Adherent Mammalian Cells", Proceedings of the National Academy of Sciences, vol. 90, No. 3, pp. 893-897, Feb. 1993.
A. L. Llamas-Saiz et al., "Double-Stranded Helical Twisted β-Sheet Channels in Crystals of Gramicidin S Grown in the Presence of Trifluoroacetic and Hydrochloric Acids", Acta Crystallographica Section D Biological Crystallograph, vol. 63, No. 3, pp. 401-407, Mar. 2007.
T. Kubo et al., "Structure and Affinity of DNA Binding Peptides", Nucleic Acids Symposium Series 2000, No. 44, pp. 49-50, 2000.

(Continued)

*Primary Examiner* — Janet Epps -Smith
(74) *Attorney, Agent, or Firm* — Wenderoth, Lind & Ponack, L.L.P.

(57) ABSTRACT

A method for transfecting nucleic acid to cell comprising a step for forming a nucleic acid complex by bringing a double-stranded nucleic acid molecule into contact with a nucleic acid carrier having an amino acid sequence of alternating a basic amino acid and a hydrophobic amino acid, which has a peptide chain that forms a β-sheet structure in which a side chain of a positively charged basic amino acid is disposed on one surface side and a side chain of a hydrophobic amino acid is disposed on the opposite surface side in the presence of the double-stranded nucleic acid molecule having a double helix structure, and by binding the double-stranded nucleic acid molecule and the peptide chain through either one or both of the electrostatic interaction between the side chains of the basic amino acid and phosphate groups and hydrogen bonds between the double stranded-nucleic acid molecule and the peptide chain and a nucleic acid complex used for the same are disclosed.

14 Claims, 9 Drawing Sheets

(56) References Cited

OTHER PUBLICATIONS

K. Yokoyama et al., "Amphiphilic β-Sheet Peptides Can Bind to Double and Triple Stranded DNA", Nucleosides, Nucleotides & Nucleic Acids, vol. 20, No. 4-7, pp. 1317-1320, 2001 (Abstract only).
K. Nakashima et al., "Outstanding Bio-Related Experiment Series, Gene Transfer and Gene Expression Analysis Protocol, Providing a simple and versatile gene transfer method and an expression-analysis method according to the purpose", published by Youdo-Sha, Sep. 2003, ISBN 9784897064116.
Office Action issued Oct. 17, 2014 in corresponding Chinese Patent Application No. 201180034113.8 with English translation.
Office Action issued Feb. 7, 2014 in corresponding Chinese Application No. 201180034113.8.
T. Kubo et al., "Controlled Intracellular Localization and Enhanced Antisense Effect of Oligonucleotides by Chemical Conjugation", Org. Biomol. Chem., vol. 3, pp. 3257-3259, 2005.
Communication pursuant to Article 94(3) EPC issued Mar. 3, 2015 in corresponding European Patent Application No. 11806691.9.
Allen et al., "A novel node of DNA recognition by β-sheet revealed by the solution structure of the GCC-box binding domain in complex with DNA", The EMBO Journal, vol. 17, No. 18, pp. 5484-5496, 1998.

* cited by examiner

SEQUENCE LISTING

<160> NUMBER OF SEQ ID NOS: 36

<210> SEQ ID NO 1
<211> LENGTH: 9
<212> TYPE: PRT
<213> ORGANISM: Artificial
<220> FEATURE:
<223> OTHER INFORMATION: NLS sequence of human nucleoprasmin

```
<400> SEQUENCE: 1

Gln Ala Lys Lys Lys Lys Leu Asp Lys
1               5

<210> SEQ ID NO 2
<211> LENGTH: 8
<212> TYPE: PRT
<213> ORGANISM: Artificial
<220> FEATURE:
<223> OTHER INFORMATION: NLS sequence of human p53

<400> SEQUENCE: 2

Ser Pro Gln Pro Lys Lys Lys Pro
1               5

<210> SEQ ID NO 3
<211> LENGTH: 12
<212> TYPE: PRT
<213> ORGANISM: Artificial
<220> FEATURE:
<223> OTHER INFORMATION: NLS sequence of HIV-1 Rev protein

<400> SEQUENCE: 3

Arg Gln Ala Arg Arg Asn Arg Arg Arg Arg Trp Arg
1               5                   10

<210> SEQ ID NO 4
<211> LENGTH: 8
<212> TYPE: PRT
<213> ORGANISM: Artificial
<220> FEATURE:
<223> OTHER INFORMATION: NLS sequence of SV40 T-antigen

<400> SEQUENCE: 4

Gly Pro Lys Lys Lys Arg Lys Val
1               5

<210> SEQ ID NO 5
<211> LENGTH: 12
<212> TYPE: PRT
<213> ORGANISM: Artificial
<220> FEATURE:
<223> OTHER INFORMATION: NLS sequence of Influenza virus nucleoplasmin

<400> SEQUENCE: 5

Asn Ser Ala Ala Phe Glu Asp Leu Arg Val Leu Ser
1               5                   10

<210> SEQ ID NO 6
<211> LENGTH: 18
<212> TYPE: PRT
<213> ORGANISM: Artificial
<220> FEATURE:
<223> OTHER INFORMATION: NLS sequence of Antennapedia Penetratin

<400> SEQUENCE: 6

Arg Gln Ile Lys Ile Trp Phe Gln Asn Arg Arg Met Lys Trp Lys Lys
1               5                   10                  15

Glu Asn

<210> SEQ ID NO 7
<211> LENGTH: 14
<212> TYPE: PRT
<213> ORGANISM: Artificial
<220> FEATURE:
```

```
<223> OTHER INFORMATION: NLS sequence of HIV-1 Tat protein

<400> SEQUENCE: 7

Gly Arg Lys Lys Arg Arg Gln Arg Arg Pro Pro Gln Gly
1               5                   10

<210> SEQ ID NO 8
<211> LENGTH: 9
<212> TYPE: PRT
<213> ORGANISM: Artificial
<220> FEATURE:
<223> OTHER INFORMATION: NES sequence of HIV-1 Rev protein

<400> SEQUENCE: 8

Leu Pro Pro Leu Glu Arg Leu Thr Leu
1               5

<210> SEQ ID NO 9
<211> LENGTH: 13
<212> TYPE: PRT
<213> ORGANISM: Artificial
<220> FEATURE:
<223> OTHER INFORMATION: NES sequence of MAPKK

<400> SEQUENCE: 9

Ala Leu Gln Lys Lys Leu Glu Glu Leu Glu Leu Asp Glu
1               5                   10

<210> SEQ ID NO 10
<211> LENGTH: 10
<212> TYPE: PRT
<213> ORGANISM: Artificial
<220> FEATURE:
<223> OTHER INFORMATION: NES sequence of PKI-alpha

<400> SEQUENCE: 10

Leu Ala Leu Lys Leu Ala Gly Leu Asp Ile
1               5                   10

<210> SEQ ID NO 11
<211> LENGTH: 13
<212> TYPE: PRT
<213> ORGANISM: Artificial
<220> FEATURE:
<223> OTHER INFORMATION: NES sequence of Dsk-1

<400> SEQUENCE: 11

Ser Leu Glu Gly Ala Val Ser Glu Ile Ser Leu Arg Asp
1               5                   10

<210> SEQ ID NO 12
<211> LENGTH: 9
<212> TYPE: PRT
<213> ORGANISM: Artificial
<220> FEATURE:
<223> OTHER INFORMATION: NES sequence of TFIIIA

<400> SEQUENCE: 12

Leu Pro Val Leu Glu Asn Leu Thr Leu
1               5

<210> SEQ ID NO 13
<211> LENGTH: 10
<212> TYPE: PRT
<213> ORGANISM: Artificial
<220> FEATURE:
<223> OTHER INFORMATION: NES sequence of Matrin3
```

<400> SEQUENCE: 13

Leu Ala Ser Leu Met Asn Leu Gly Met Ser
1               5                   10

<210> SEQ ID NO 14
<211> LENGTH: 10
<212> TYPE: PRT
<213> ORGANISM: Artificial
<220> FEATURE:
<223> OTHER INFORMATION: 5mer of Arg-Leu

<400> SEQUENCE: 14

Arg Leu Arg Leu Arg Leu Arg Leu Arg Leu
1               5                   10

<210> SEQ ID NO 15
<211> LENGTH: 12
<212> TYPE: PRT
<213> ORGANISM: Artificial
<220> FEATURE:
<223> OTHER INFORMATION: 6mer of Arg-Leu

<400> SEQUENCE: 15

Arg Leu Arg Leu Arg Leu Arg Leu Arg Leu Arg Leu
1               5                   10

<210> SEQ ID NO 16
<211> LENGTH: 14
<212> TYPE: PRT
<213> ORGANISM: Artificial
<220> FEATURE:
<223> OTHER INFORMATION: 7mer of Arg-Leu

<400> SEQUENCE: 16

Arg Leu Arg Leu Arg Leu Arg Leu Arg Leu Arg Leu Arg Leu
1               5                   10

<210> SEQ ID NO 17
<211> LENGTH: 16
<212> TYPE: PRT
<213> ORGANISM: Artificial
<220> FEATURE:
<223> OTHER INFORMATION: 8mer of Arg-Leu

<400> SEQUENCE: 17

Arg Leu Arg Leu Arg Leu Arg Leu Arg Leu Arg Leu Arg Leu Arg Leu
1               5                   10                  15

<210> SEQ ID NO 18
<211> LENGTH: 18
<212> TYPE: PRT
<213> ORGANISM: Artificial
<220> FEATURE:
<223> OTHER INFORMATION: 9mer of Arg-Leu

<400> SEQUENCE: 18

Arg Leu Arg Leu Arg Leu Arg Leu Arg Leu Arg Leu Arg Leu Arg Leu
1               5                   10                  15

Arg Leu

<210> SEQ ID NO 19
<211> LENGTH: 20
<212> TYPE: PRT
<213> ORGANISM: Artificial
<220> FEATURE:

```
<223> OTHER INFORMATION: 10mer of Arg-Leu

<400> SEQUENCE: 19

Arg Leu Arg Leu Arg Leu Arg Leu Arg Leu Arg Leu Arg Leu Arg Leu
1               5                   10                  15

Arg Leu Arg Leu
            20

<210> SEQ ID NO 20
<211> LENGTH: 25
<212> TYPE: PRT
<213> ORGANISM: Artificial
<220> FEATURE:
<223> OTHER INFORMATION: NLS-(RL)7

<400> SEQUENCE: 20

Gln Ala Lys Lys Lys Lys Leu Asp Lys Arg Leu Arg Leu Arg Leu Arg
1               5                   10                  15

Leu Arg Leu Arg Leu Arg Leu Gly Lys
            20                  25

<210> SEQ ID NO 21
<211> LENGTH: 24
<212> TYPE: PRT
<213> ORGANISM: Artificial
<220> FEATURE:
<223> OTHER INFORMATION: NLS-(RL)7

<400> SEQUENCE: 21

Ser Pro Gln Pro Lys Lys Lys Pro Arg Leu Arg Leu Arg Leu Arg Leu
1               5                   10                  15

Arg Leu Arg Leu Arg Leu Gly Lys
            20

<210> SEQ ID NO 22
<211> LENGTH: 28
<212> TYPE: PRT
<213> ORGANISM: Artificial
<220> FEATURE:
<223> OTHER INFORMATION: NLS-(RL)7

<400> SEQUENCE: 22

Arg Gln Ala Arg Arg Asn Arg Arg Arg Trp Arg Arg Leu Arg Leu Arg
1               5                   10                  15

Leu Arg Leu Arg Leu Arg Leu Arg Leu Gly Lys
            20                  25

<210> SEQ ID NO 23
<211> LENGTH: 24
<212> TYPE: PRT
<213> ORGANISM: Artificial
<220> FEATURE:
<223> OTHER INFORMATION: NLS-(RL)7

<400> SEQUENCE: 23

Gly Pro Lys Lys Lys Arg Lys Val Arg Leu Arg Leu Arg Leu Arg Leu
1               5                   10                  15

Arg Leu Arg Leu Arg Leu Gly Lys
            20

<210> SEQ ID NO 24
<211> LENGTH: 28
<212> TYPE: PRT
<213> ORGANISM: Artificial
```

```
<220> FEATURE:
<223> OTHER INFORMATION: NLS-(RL)7

<400> SEQUENCE: 24

Asn Ser Ala Ala Phe Glu Asp Leu Arg Val Leu Ser Arg Leu Arg Leu
1               5                   10                  15

Arg Leu Arg Leu Arg Leu Arg Leu Arg Leu Gly Lys
            20                  25

<210> SEQ ID NO 25
<211> LENGTH: 30
<212> TYPE: PRT
<213> ORGANISM: Artificial
<220> FEATURE:
<223> OTHER INFORMATION: NLS-(RL)7

<400> SEQUENCE: 25

Gly Arg Lys Lys Arg Arg Gln Arg Arg Pro Pro Gln Gly Arg Leu
1               5                   10                  15

Arg Leu Arg Leu Arg Leu Arg Leu Arg Leu Arg Leu Gly Lys
            20                  25                  30

<210> SEQ ID NO 26
<211> LENGTH: 29
<212> TYPE: PRT
<213> ORGANISM: Artificial
<220> FEATURE:
<223> OTHER INFORMATION: NES-(RL)7

<400> SEQUENCE: 26

Leu Pro Pro Leu Glu Arg Leu Thr Leu Gly Gly Gly Gly Arg Leu Arg
1               5                   10                  15

Leu Arg Leu Arg Leu Arg Leu Arg Leu Gly Lys
            20                  25

<210> SEQ ID NO 27
<211> LENGTH: 33
<212> TYPE: PRT
<213> ORGANISM: Artificial
<220> FEATURE:
<223> OTHER INFORMATION: NES-(RL)7

<400> SEQUENCE: 27

Ala Leu Gln Lys Lys Leu Glu Glu Leu Glu Leu Asp Glu Gly Gly
1               5                   10                  15

Gly Arg Leu Arg Leu Arg Leu Arg Leu Arg Leu Arg Leu Arg Leu Gly
            20                  25                  30

Lys

<210> SEQ ID NO 28
<211> LENGTH: 30
<212> TYPE: PRT
<213> ORGANISM: Artificial
<220> FEATURE:
<223> OTHER INFORMATION: NES-(RL)7

<400> SEQUENCE: 28

Leu Ala Leu Lys Leu Ala Gly Leu Asp Ile Gly Gly Gly Gly Arg Leu
1               5                   10                  15

Arg Leu Arg Leu Arg Leu Arg Leu Arg Leu Arg Leu Gly Lys
            20                  25                  30

<210> SEQ ID NO 29
```

-continued

```
<211> LENGTH: 33
<212> TYPE: PRT
<213> ORGANISM: Artificial
<220> FEATURE:
<223> OTHER INFORMATION: NES-(RL)7

<400> SEQUENCE: 29

Ser Leu Glu Gly Ala Val Ser Glu Ile Ser Leu Arg Asp Gly Gly
1               5                   10                  15

Gly Arg Leu Arg Leu Arg Leu Arg Leu Arg Leu Arg Leu Arg Leu Gly
            20                  25                  30

Lys

<210> SEQ ID NO 30
<211> LENGTH: 29
<212> TYPE: PRT
<213> ORGANISM: Artificial
<220> FEATURE:
<223> OTHER INFORMATION: NES-(RL)7

<400> SEQUENCE: 30

Leu Pro Val Leu Glu Asn Leu Thr Leu Gly Gly Gly Gly Arg Leu Arg
1               5                   10                  15

Leu Arg Leu Arg Leu Arg Leu Arg Leu Arg Leu Gly Lys
            20                  25

<210> SEQ ID NO 31
<211> LENGTH: 30
<212> TYPE: PRT
<213> ORGANISM: Artificial
<220> FEATURE:
<223> OTHER INFORMATION: NES-(RL)7

<400> SEQUENCE: 31

Leu Ala Ser Leu Met Asn Leu Gly Met Ser Gly Gly Gly Arg Leu
1               5                   10                  15

Arg Leu Arg Leu Arg Leu Arg Leu Arg Leu Arg Leu Gly Lys
            20                  25                  30

<210> SEQ ID NO 32
<211> LENGTH: 21
<212> TYPE: DNA
<213> ORGANISM: Artificial
<220> FEATURE:
<223> OTHER INFORMATION: siRNA against hTERT in Jurkat cell line

<400> SEQUENCE: 32
ggagcaaguu gcaaagcaut t                                            21

<210> SEQ ID NO 33
<211> LENGTH: 21
<212> TYPE: DNA
<213> ORGANISM: Artificial
<220> FEATURE:
<223> OTHER INFORMATION: siRNA against hTERT in Hela cell line

<400> SEQUENCE: 33
augcuuugca acuugcucct t                                            21

<210> SEQ ID NO 34
<211> LENGTH: 21
<212> TYPE: DNA
<213> ORGANISM: Artificial
<220> FEATURE:
<223> OTHER INFORMATION: siRNA against Bcr/abl in K562 cell line
```

```
<400> SEQUENCE: 34
gcagaguuca aaagcccuut t                                              21

<210> SEQ ID NO 35
<211> LENGTH: 21
<212> TYPE: DNA
<213> ORGANISM: Artificial
<220> FEATURE:
<223> OTHER INFORMATION: siRNA against Bcr/abl in K562 cell line

<400> SEQUENCE: 35
aacggcuuuu gaacucugct t                                              21

<210> SEQ ID NO 36
<211> LENGTH: 24
<212> TYPE: PRT
<213> ORGANISM: Artificial
<220> FEATURE:
<223> OTHER INFORMATION: LRALLRALLRALLRALLRALLRAL

<400> SEQUENCE: 36

Leu Arg Ala Leu Leu Arg Ala Leu Leu Arg Ala Leu Leu Arg Ala Leu
1               5                   10                  15

Leu Arg Ala Leu Leu Arg Ala Leu
            20
```

METHOD FOR TRANSFECTING NUCLEIC ACID TO CELL AND NUCLEIC ACID COMPLEX

This application is a U.S. national stage of International Application No. PCT/JP2011/065612 filed Jul. 7, 2011.

TECHNICAL FIELD

The present invention relates to an improvement on a method for transfecting double-stranded nucleic acid molecule to target cell and a nucleic acid carrier used for that, and a nucleic acid complex obtained from the nucleic acid carrier and the double-stranded nucleic acid molecule.

BACKGROUND ART

RNA interference (RNAi) is a phenomenon in which expression of specific gene is reduced by base sequence specific destruction of mRNA triggered by small double-stranded RNA having base length of 21 to 25 (siRNA) and its application to medication is strongly expected because of its higher efficiency and base sequence specificity than an antisense nucleic acid which is in a drug trial stage. However, there are still many problems to be solved, such as transfection of siRNA to cell, assurance of safety and prolonged inhibitory effect in the cells.

Transfection of poly-(oligo)nucleotide including siRNAs into cell is difficult since they are polyanionic, which have low affinity for hydrophobic cell membrane.

Also, protection form nucleases that exist in cells to destroy exogenous nucleic acids is required to assure the safety and the prolonged inhibitory effect in the cells. Various methods are proposed so far, which are classified into the methods using a virus vector and the ones not using it.

Virus vectors are virus lack of replicative capability. The method for transferring gene into cell using the virus vector has the advantage that the processes of transfection into cell to protein synthesis may be carried out efficiently by taking the advantage of pattern of growth of virus. Recombinant virus vectors derived from adenovirus, retrovirus, lentivirus, adeno-associated virus and the like (for example, see Patent Document 1 and Non-patent Document 1). However, it has been pointed out that the method using the virus vector may cause cancer because of the virus used and some examples of death have been confirmed. Also, there is the problem of the inactivation because of the production of virus neutralizing antibody and the difficulties in the large-scale production and quality control.

On the other hand, various methods including calcium phosphate method, electroporation method, liposome method, lipofectin method, microinjection method, hydrodynamic method, the methods using complexes of carrier such as antibody and peptide and nucleic acid as the method for transfecting the nucleic acid into the target cell without using the virus vector (for example, see Non-patent Document 1).

However, conventional method for transfecting nucleic acid is yet insufficient for producing a gene medicine that introduces the nucleic acid such as siRNA in cells. In other words, novel nucleic acid carrier that has high efficiency and high reproducibility in the transfection of nucleic acids regardless of cell types, improved resistance against intracellular nuclease, sequence-specific binding and high affinity to the target nucleic acid and low cytotoxicity is needed.

A number of nucleic acid carriers and methods for transfecting nucleic acid to cell have been developed so far, and, in particular, the nucleic acid carriers and the methods for transfecting nucleic acid in cells using functional peptide such as intracellular signal peptide are attracting attention. For example, such nucleic acid carriers and methods include a method for transfecting anionic nucleic acids to cell using nuclear localization signal peptides (for example, see Patent-Documents 2 and 3), other signal peptides (for example, see Patent Document 4), and design peptide (for example, see Patent Document 5); a nucleic acid carrier having improved cell specificity using sugar-modified peptide (for example, see Patent Document 6), a functional molecule in which an amphiphilic polymer and peptide are linked (for example, see Patent Document 7), and a method in which conventional nucleic acid carrier is used with peptide (for example, see Patent Document 8).

PRIOR ART DOCUMENTS

Patent Documents

Patent Document 1: Japanese published unexamined application No. 1998-146191.
Patent Document 2: Japanese published unexamined application No. 2003-514564.
Patent Document 3: Japanese published unexamined application No. 2001-288200.
Patent Document 4: Japanese published unexamined application No. 1998-506001.
Patent Document 5: Japanese published unexamined application No. 2002-316997.
Patent Document 6: Japanese published unexamined application No. 1999-290073.
Patent Document 7: Japanese published unexamined application No. 2003-503370
Patent Document 8: Japanese published unexamined application No. 2004-65238.

Non-Patent Documents

Non-Patent Document 1: Eds., Kazunori Nakajima and Yoshihiro Kitamura, "Kanarazu umaku iku idenshi donyu to hatugen kaiseki purotokoru" (Protocols that works well for gene transfection and expression analysis), September, 2003, Yodosha, Tokyo, Japan, ISBN 9784897064116.

SUMMARY OF THE INVENTION

Problem to be Solved by the Invention

As mentioned above, a number of nucleic acid carriers and methods for transfecting nucleic acid to cell have been developed so far. However, none of these have been established yet. Since most of these carriers and methods target at DNA, they are not necessarily suitable for transfecting siRNA, which has low molecular weight and is more labile than DNA to cell.

Under these circumstances, the object of present invention is to provide a method for transfecting double-stranded nucleic acid molecule to target cell that makes possible to introduce double-stranded RNAs such as siRNA efficiently to target cells and provides improved resistance against intracellular nuclease and has low adversed effect because of cytotoxicity and a nucleic acid carrier, and a nucleic acid complex.

Means to Solve the Problem

The first aspect of the present invention solves the aforementioned problem by providing method for transfecting nucleic acid to cell described in (1) to (9) as follows.

(1) A method for transfecting nucleic acid to cell comprising a step for forming a nucleic acid complex by bringing a double-stranded nucleic acid molecule into contact with a nucleic acid carrier having an amino acid sequence of alternating a basic amino acid and a hydrophobic amino acid, which has a peptide chain that forms a β-sheet structure in which a side chain of a positively charged basic amino acid is disposed on one surface side and a side chain of a hydrophobic amino acid is disposed on the opposite surface side in the presence of the double-stranded nucleic acid molecule having a double helix structure, and by binding the double-stranded nucleic acid molecule and the peptide chain through either one or both of the electrostatic interaction between the side chains of the basic amino acid and phosphate groups and hydrogen bonds between the double stranded-nucleic acid molecule and the peptide chain, and a step for transfecting the nucleic acid complex to cell.

(2) The method for transfecting nucleic acid to cell according to (1) wherein the basic amino acid is selected from the group consisting essentially of arguable, lysine and ornithine and the hydrophobic amino acid is selected from the group consisting essentially of leucine, isoleucine and tryptophane.

(3) The method for transfecting nucleic acid to cell according to (1) or (2) wherein the peptide chain has an amino acid sequence represented by any one of $(RL)_n$ and $(LR)_n$ (wherein R and L represent argine residue and leucine residue, respectively and n represents an integer of 5 to 20).

(4) The method for transfecting nucleic acid to cell according to any one of (1) to (3) wherein the molar ratio of the double-stranded nucleic acid molecule and the nucleic acid carrier in the step for forming a nucleic acid complex is 1:4 to 1:30.

(5) The method for transfecting nucleic acid to cell according to any one of (1) to (4) wherein the double-stranded nucleic acid molecule is siRNA.

(6) The method for transfecting nucleic acid to cell according to any one of (1) to (5) wherein the nucleic acid complex has the localization activity toward the target cell and/or the specific site thereof.

(7) The method for transfecting nucleic acid to cell according to (6) wherein a signal peptide having a localizing activity toward the target cell and/or a portion thereof is bound to at least a portion of the double-stranded nucleic acid molecule or the nucleic acid carrier.

(8) The method for transfecting nucleic acid to cell according to (7) wherein the signal peptide has an amino acid sequence represented by any one of SEQ ID No. 1 to 13 as follows.

QAKKKKLDK [SEQ ID No. 1]

SPQPKKKP [SEQ ID No. 2]

RQARRNRRRWR [SEQ ID No. 3]

GPKKKRKV [SEQ ID No. 4]

NSAAFEDLRVLS [SEQ ID No. 5]

RQIKIWFQNRRMKWKKEN [SEQ ID No. 6]

GRKKRRQRRRPPQG [SEQ ID No. 7]

LPPLERLTL [SEQ ID No. 8]

ALQKKLEELELDE [SEQ ID No. 9]

LALKLAGLDI [SEQ ID No. 10]

SLEGAVSEISLRD [SEQ ID No. 11]

LPVLENLTL [SEQ ID No. 12]

LASLMNLGMS [SEQ ID No. 13]

(9) The method for transfecting nucleic acid to cell according to (7) or (8) wherein a terminal of the signal peptide is bound to a peptide chain of the nucleic acid carrier or a terminal of the double-stranded nucleic acid.

The second aspect of the present invention solves the aforementioned problem by providing nucleic acid complex described in (10) to (16) as follows.

(10) A nucleic acid complex in which a nucleic acid carrier having an amino acid sequence of alternating a basic amino acid and a hydrophobic amino acid, which has a peptide chain that forms a β-sheet structure in which a side chain of a positively charged basic amino acid is disposed on one surface side and a side chain of a hydrophobic amino acid is disposed on the opposite surface side in the presence of a double-stranded nucleic acid molecule having a double helix structure, and the double-stranded nucleic acid molecule are bound through the electrostatic interaction between the side chains of the basic amino acid and phosphate groups.

(11) The nucleic acid complex according to (10) wherein the basic amino acid is selected from the group consisting essentially of arginine, lysine and ornithine and the hydrophobic amino acid is selected from the group consisting essentially of leucine, isoleucine and tryptophane.

(12) The nucleic acid complex according to (10) or (11) wherein the peptide chain has an amino acid sequence represented by any one of $(RL)_n$ and $(LR)_n$ (wherein R and L represent argine residue and leucine residue, respectively and n represents an integer of 5 to 20).

(13) The nucleic acid complex according to any one of (10) to (12) wherein the double-stranded nucleic acid molecule is siRNA.

(14) The nucleic acid complex according to any one of (10) to (13) wherein a signal peptide having a localizing activity toward the target cell and/or a portion thereof is bound to at least a portion of the double-stranded nucleic acid molecule or the nucleic acid carrier.

(15) The nucleic acid complex according to (14) wherein the signal peptide has an amino acid sequence represented by any one of SEQ ID No. 1 to 13 as above.

(16) The nucleic acid complex according to (14) or (15) wherein a terminal of the signal peptide is bound to a peptide chain of the nucleic acid earner or a terminal of the double-stranded nucleic acid.

Effect of the Invention

The nucleic carrier of the present invention has the peptide chain that forms a β-sheet structure in which a side chain of a positively charged basic amino acid is disposed on one surface side and a side chain of a hydrophobic amino acid is disposed on the opposite surface side in the presence of a double-stranded nucleic acid molecule having a double helix structure. It is reported that the peptide chain that forms a β-sheet structure may bind with double-stranded nucleic acid such as double-stranded DNA thorough hydrogen bonds between the double-stranded nucleic acid molecule and the peptide and the like (for example, see *Proc. Natl. Acad. Sci. USA*, vol. 74 (1977), p. 1458-1462). As basic and hydrophobic amino acids in the peptide chain of the nucleic carrier of the present invention alternate with each other, when it forms the β-sheet structure, the side chain of positively charged basic amino acids are disposed on one surface side of the β-sheet structure with intervals of about 7 nm, which is almost equal to those between phosphate moieties in the nucleotide chain. Therefore, the nucleic acid carrier of the present invention binds with the double-stranded nucleic acid molecule such as double-stranded DNA and double-stranded RNA on the peptide chain portion that forms the β-sheet structure through either one or both of the electrostatic interaction between the sides chains of the basic amino acid and phosphate groups and hydrogen bonds between the double stranded-nucleic acid molecule and the peptide chain. With these, the resistance against nuclease of the double-stranded nucleic acid molecule may be significantly improved and permeability through lipid bilayer cell membrane may be increased as well because the side chain of the hydrophobic amino acids is exposed outside of the complex, which results in increased transfection efficiency of the double-stranded nucleic acid molecule in cells. Also, the affinity and the base sequence specificity of the nucleic carrier to the double-stranded nucleic acid molecule may be improved by choosing the amino acid sequence of the peptide chain. Since the nucleic acid carrier of the present invention, which is based on polypeptide has low cytotoxicity, adverse effect may be reduced when it is applied to gene therapy and gene medicine. Moreover, control of localization in cells and improvement of the cell specificity may be achieved by, for example, modifying with signal peptide, by which various functions may be provided such as increased transfection efficiency of the nucleic acid and reduced adverse effect in the gene therapy.

Since the double-stranded nucleic acid molecule is introduced using the nucleic acid carrier that has features described above in the method for transfecting nucleic acid in cell of the present invention, the method has the advantage that the double-stranded nucleic acid molecule such as siRNA may be introduced efficiently in target cell, high resistance against nuclease may be provided to the double-stranded nucleic acid molecule, and has low risk of adverse effect due to low cytotoxicity. In addition, the nucleic acid complex of the present invention may introduce the double-stranded nucleic acid such as siRNA efficiently in target cell acid has high resistance against nuclease. Moreover, it has low cytotoxicity since it is based on polypeptide, which makes adverse effect lower when it is applied to gene therapy and gene medicine and preferably applicable to these applications.

EMBODIMENT OF THE INVENTION

Figure 1:
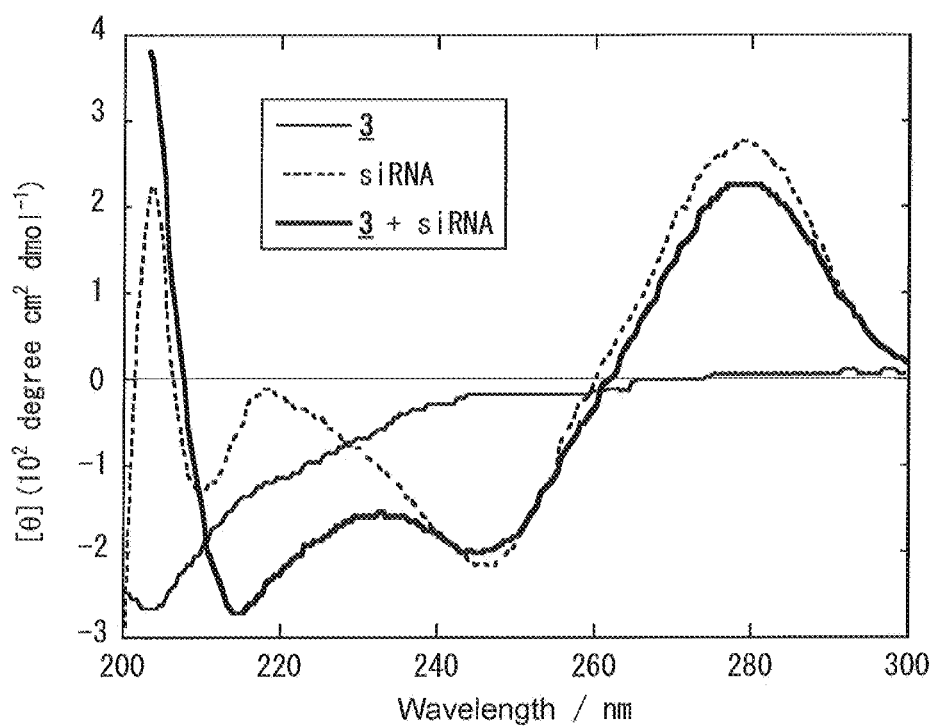
FIG. 1 shows circular dichromic (CD) spectra of siRNA, nucleic acid carrier (RL)$_7$ and nucleic acid complex.

Hereinafter embodiment of the present invention will be explained so as to help understanding the present invention.

The method for transfecting nucleic acid to cell according to first embodiment of the present invention (hereinafter may be abbreviated to "the method for transfecting nucleic acid to cell" or the "present method") comprising a step for forming a nucleic acid complex by bringing a double-stranded nucleic acid molecule into contact with a nucleic acid carrier having an amino acid sequence of alternating a basic amino acid and a hydrophobic amino acid, which has a peptide chain that forms a β-sheet structure in which a side chain of a positively charged basic amino acid is disposed on one surface side and a side chain of a hydrophobic amino acid is disposed on the opposite surface side in the presence of the double-stranded nucleic acid molecule having a double helix structure, and by binding the double-stranded nucleic acid molecule and the peptide chain through either one or both of the electrostatic interaction between the side chains of the basic amino acid and phosphate groups and hydrogen bonds between the double stranded-nucleic acid molecule and the peptide chain, and a step for transfecting the nucleic acid complex to cell.

At first, the nucleic acid carrier used for the present method (hereinafter may be abbreviated to "the nucleic acid carrier") and the nucleic acid complex according to the second embodiment of the present invention (hereinafter may be abbreviated to "the nucleic acid complex" or "complex") will be illustrated in more detail.

(1) Nucleic Acid Carrier

The nucleic acid carrier has the peptide chain having an amino acid sequence of alternating a basic amino acid and a hydrophobic amino acid, which has a peptide chain that forms a β-sheet structure in which a side chain of a positively charged basic amino acid is disposed on one surface side and a side chain of a hydrophobic amino acid is disposed on the opposite surface side in the presence of the double-stranded nucleic acid molecule having a double helix structure. As mentioned above, the peptide chain that forms a β-sheet structure may form the complex with double-stranded nucleic acid such as double-stranded DNA (dsDNA). In particular, when the peptide chain forms the second structure in which a side chain of the positively charged basic amino acid is disposed on one surface side and the side chain of a hydrophobic amino acid is disposed on the opposite side of the sheet structure, it may bind to the double-stranded nucleic acid molecule through either one or both of the electrostatic interaction between the side chains of the basic amino acid and phosphate groups and hydrogen bonds between the double stranded-nucleic acid molecule and the peptide chain. In the nucleic acid complex thus formed, as the side chain of the hydrophobic amino acids is exposed outside of the complex, the affinity of the nucleic acid complex to lipid bilayer cell membrane increases and the transfection efficiency of the double-stranded nucleic acid molecule in cells is improved.

The amino acid sequence of the peptide chain is not particularly limited so far as it fulfills the aforementioned requirement, that is, it has the amino acid sequence of alternating a basic amino acid and a hydrophobic amino acid, which has a peptide chain that forms a β-sheet structure in which a side chain of a positively charged basic amino acid is disposed on one surface side and a side chain of a hydrophobic amino acid is disposed on the opposite surface side in the presence of the double-stranded nucleic acid molecule having a double helix structure and it may form strong binding with the double-stranded nucleic acid molecule through either one or both of the electrostatic interaction between the side chains of the basic amino acid and phosphate groups and hydrogen bonds between the double stranded-nucleic acid molecule and the peptide chain. Also, the β-sheet structure may be either parallel β-sheet structure or anti-parallel β-sheet structure so far as it fulfills the aforementioned requirement.

Formation of the β-sheet structure may be confirmed by any known methods in the art such as circular dichromic (CD) spectroscopy.

Preferable amino acid sequence of the peptide chain includes the amino acid sequence of alternating a basic amino acid selected from the group consisting essentially of arginine, lysine and ornithine and a hydrophobic amino acid selected from the group consisting essentially of leucine, isoleucine, valine and tryptophane. Length of the peptide chain may be selected depending on the chain length of the double-stranded nucleic acid molecule, that is, the number of phosphate groups (negative charge) of the double-stranded nucleic acid molecule that forms the complex and the like. When the length of the peptide chain is too short compared with the double-stranded nucleic acid molecule, stable complex cannot be obtained and the protecting effect of the double-stranded nucleic acid molecule against nuclease. On the other hand, when the length of the peptide chain is too short compared with the double-stranded nucleic acid molecule, transfection efficiency of the nucleic acid to cell will be reduced because of the positive charge of the basic amino acid residues.

More preferable amino acid sequence of the peptide chain includes the amino acid sequence represented by any one of $(RL)_n$ and $(LR)_n$. Here, R and L represent argine residue and leucine residue, respectively. Arginine (R) residue has guanidyl group as basic group, which is preferred for forming stable complex since it may strongly interact with phosphate group as shown in the chemical formula below

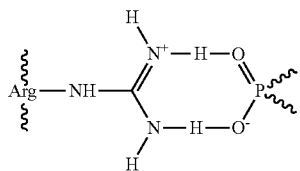

Moreover, n is an integer representing the number repeat of the unit RL or LR, which may be selected depending on the chain length of the double-stranded nucleic acid molecule, that is, the number of phosphate groups (negative charge) of the double-stranded nucleic acid molecule that forms the complex and the like. When the double-stranded nucleic acid molecule is siRNA, n is, for example natural number of 5 or more, preferably 5 to 20, more preferably 7 to 10. When n is less than 5, it hardly forms stable complex with the double-stranded nucleic acid molecule, whereas n is too large, problems of cytotoxicity, imperfect neutralization of the negative charge of phosphate groups may arise.

The nucleic acid carrier preferably has the localization activity toward the target cell and/or its specific site or organelle (subcellular organelle). The target cell or its specific site or organelle to be target by the nucleic acid complex for localization may be selected depending on the kind of the double-stranded nucleic acid molecule to be introduced to the target cell and the function in the cell and the like.

Any known means in the art may be used for the means to provide localizing activity to the nucleic acid complex depending on the target cell or its specific site or organelle to be target by the nucleic acid complex for localization. Particular example of the means to provide localizing activity toward the target cell to the nucleic acid complex includes, for example, linking a ligand which binds to a receptor specifically appears on the target cell to the nucleic acid carrier. Particular example of the means to provide localizing activity toward specific site or organelle of the target cell to the nucleic add complex includes linking a signal peptide having the localization activity toward the specific site or organelle of the target cell to the nucleic acid carrier. Particular examples of the signal peptide that can be linked include various nuclear localization signal (NLS) peptide and nuclear export signal (NES) peptides and the like.

Inportin, a transfer protein and Ran, a GTP-binding protein bind to the NLS, which is recognized by nuclear pore complex and transferred from the plasma to nucleus. Thus, the localization to the nucleus may be achieved. Particular examples of NLS include the peptide having the amino acid sequence represented by SEQ ID No. 1-7 as shown below.

```
                                           [SEQ ID No. 1]
QAKKKKLDK
(NLS sequence from Nucleoplasmin)

[SEQ ID No. 2]
SPQPKKKP
(NLS sequence from human p53)

[SEQ ID No. 3]
RQARRNRRRRWR
(NLS sequence from HIV-1 Rev protein)

[SEQ ID No. 4]
GPKKKRKV
(NLS sequence from SV40T antibody)

[SEQ ID No. 5]
NSAAFEDLRVLS
(NLS sequence from Influenza virus nucleoprotein)

[SEQ ID No. 6]
RQIKIWFQNRRMKWKKEN
(NLS sequence from Antennapadia penetratin)

[SEQ ID No. 7]
GRKKRRQRRRPPQG
NLS sequence from HIV-1 Tat protein)
```

CRM1, a transfer protein and Ran, a GTP-binding protein bind to the NES, which is recognized by nuclear pore complex and transferred from the nucleus to plasma. Thus, the transfer from the nucleus to the plasma may be achieved.

Particular examples of NES include the peptide having the amino acid sequence represented by SEQ ID No. 8-13 as shown below.

```
                                           [SEQ ID No. 8]
    LPPLERLTL
    (NES sequence from HIV-1 Rev protein)

[SEQ ID No. 9]
    ALQKKLEELELDE
    (NES sequence from MAPKK)

[SEQ ID No. 10]
    LALKLAGLDI
    (NES sequence from PKI-α)

[SEQ ID No. 11]
    SLEGAVSEISLRD
    (NES sequence from Dsk-1)

[SEQ ID No. 12]
    LPVLENLTL
    (NES sequence from TFA IIIA)

[SEQ ID No. 13]
    LASLMNLGMS
    (NES sequence from Matrin3)
```

These signal peptides, so far as they do not inhibit the complex to form and to be introduced to the cell, they may be linked to any position of the nucleic acid carrier, for example, N- or C-terminal, or side chain so far as they do not inhibit the formation of the β-sheet structure, of the polypeptide chain that binds to the double-stranded nucleic acid molecule. Alternately, the signal peptide may be linked to the double-stranded nucleic acid molecule on both of N- and C-terminal. It is preferred that the signal peptide is linked to N-terminal of the polypeptide chain of the nucleic acid carrier that binds to the double-stranded, nucleic acid molecule. The polypeptide chain that binds to the double-stranded nucleic acid molecule and the signal peptide may be linked either directly or via appropriate spacer molecule. Example of the linker molecule includes alkylene group, polyoxyethylene group and oligopeptide and the like.

Functional molecules other than the ligand that binds to the receptor on the target cell and the signal peptide may be bound to the nucleic acid carrier. Particular example of such functional molecule includes long-chain alkyl group and lipid molecule introduced to increase the affinity to the cell membrane.

As the nucleic acid carrier mainly consists of polypeptide, it has lower cytotoxicity than conventional nucleic acid carrier such as cationic liposome. Thus, adverse effect of the nucleic acid carrier applied to gene therapy and gene medicine and the nucleic acid carrier may be preferably applicable to these applications. The cytotoxicity of the nucleic acid carrier may be evaluated by the cell viability of the target cell predetermined time after transfecting the nucleic acid carrier.

(2) Nucleic Acid Complex

The nucleic acid complex may be obtained by binding the nucleic acid carrier and the double stranded nucleic acid molecule through the electrostatic interaction between the side chain of the basic amino acid of the former and the phosphate groups of the latter.

The double-stranded nucleic acid molecule may be both of DNA and RNA and the purpose of the transfection of the nucleic acid complex may be anything such as, for example, production of desired protein, trapping transcription factor recognizing double-stranded DNA by "decoy" short-chain nucleic acid (decoy method), or RNA interference (RNAi) and the like. Therefore, the double-stranded nucleic acid molecule may include double-stranded DNA coding the protein to be expressed in cells, decoy nucleic acid and siRNA. Although base length and base sequence of the double-stranded nucleic acid residue varies depending on the purpose of the transfection of the nucleic acid complex to cell, the target cell and the disease to be treated, in case of siRNA, the base length is 9 to 50 bases, preferably 15 to 30 bases and more preferably 18 to 28 bases. In human, when the number of bases is 17 or more, total number of the polynucleotide that may be obtained ($4^{17}=1.7 \times 10^{10}$) exceeds the total number of human gene ($6 \times 10^9$). Thus, inhibition of the expression of particular gene may be possible statistically.

When the amino acid sequence of the protein to be expressed or the base sequence of the target gene is known, the double-stranded nucleic acid molecule to be introduced in the target cell may be designed by means of any known methods in the art based on the sequence data obtained from the database such as GenBank, EMBL, PDB, DDBJ. Alternately, the amino acid sequence of the target protein isolated by means of any known methods in the art or the base sequence of the mRNA coding such protein is determined by any known methods in the art, based on which the double-stranded nucleic acid molecule may also be designed.

Inhibition mechanism of the expression of the target nucleic acid having the base sequence complementary to the double-stranded nucleic acid molecule to be introduced includes (1) decomposition of mRNA/polynucleotide complex by ribonuclease H that hydrolyzes RNA chain of RNA/DNA hybrid chain specifically; (2) inhibition of transcription by ribosome complex; (3) inhibition of splicing of mRNA in case that the polynucleotide targets boundary between intron and exon; (4) base sequence specific hydrolysis of mRNA through RNA interference; and (5) inhibition of transcriptional regulator and the like.

The nucleic acid complex preferably has the localization activity toward the target cell and/or its specific site or organelle (subcellular organelle). The target cell or its specific site or organelle to be target by the nucleic acid complex for localization may be selected depending on the kind of the double-stranded nucleic acid molecule to be introduced to the target cell and the function in the cell and the like.

Any known means in the art may be used for the means to provide localizing activity to the nucleic acid complex depending on the target cell or its specific site or organelle to be target by the nucleic acid complex for localization. Particular example of the means to provide localizing activity toward the target cell to the nucleic acid complex includes, for example, linking a ligand which binds to a receptor specifically appears on the target cell to the nucleic acid carrier, or to the double-stranded nucleic acid molecule. Particular example of the means to provide localizing activity toward specific site or organelle of the target cell to the nucleic acid complex includes linking the aforementioned signal peptide having the localization activity toward the specific site or organelle of the target cell to the nucleic acid carrier, or to the double-stranded nucleic acid molecule. As too many signal peptides are introduced to the nucleic acid complex may result in reduced transfection efficiency of the to cell because of the reduction of the hydrophobicity of the nucleic acid complex, the number of signal peptides introduced to the nucleic acid complex is adjusted depending on the molecular number of the double-stranded nucleic acid complex, the specific site or organelle of the target cell, molecular weight and hydrophilicity of the signal peptide. Preferably, the N- or C-terminal of the signal peptide is linked to 5'- or 3'-terminal of the double-stranded nucleic acid molecule.

Since the particular examples of the signal peptides that can be linked to the nucleic acid carrier or the double-stranded nucleic acid molecule is similar to that as mentioned above, detailed explanation is skipped.

(3) Method for Transfecting Nucleic Acid to Cell

The nucleic acid complex may be prepared using any known methods in the art, for example, by mixing the double-stranded nucleic acid molecule and the nucleic acid carrier dissolved in a buffer solution of certain pH, and standing for certain time at given temperature for given time (for example, for 30 minutes at room temperature). Preferably, the mixing ratio (molar ratio) of the double-stranded nucleic acid molecule and the nucleic acid carrier is set so that excess amount of the latter exists in order to ensure the formation of the complex. Preferred mixing ratio of the double-stranded nucleic acid molecule and the nucleic acid carrier is 1:4 to 1:30, preferably 1:10 to 1:30, more preferably 1:15 to 1:20. If desired, the nucleic acid complex may be purified to remove excess amount of the nucleic acid carrier by any known methods in the art including gel permeation chromatography, ion chromatography, reverse-phase liquid chromatography and the like.

Any known methods in the art may be used to introduce the nucleic acid complex to the target cell. For transfecting the nucleic acid gene to incubated cell in vitro, the transaction may be carried out by adding the nucleic acid complex to culture media or culture solution containing the target cell and incubating at given temperature for given time. Also, any other methods known the art such as electroporation method, calcium phosphate method, ultrasonication method and the like may be used. Administration of the nucleic acid complex to the target cell in vivo may be carried out systemically or topically by injection, infusion and the like. Evaluation of the transfection efficiency to cell may be carried out by fluorescence microscopy using fluorescently labeled double-stranded nucleic acid molecule.

The target cell to which the nucleic acid complex is introduced is not particularly limited and any cells may be selected as the target cell so far as the expression of gene may be suppressed by transfecting exogenous nucleic acid.

The method for transfecting double-stranded nucleic acid molecule to cell, the nucleic acid carrier and the nucleic acid complex may be applied to gene therapy in which the deseases are treated by transfecting defective gene to cell or fixing or treating defection of dysfunctional cell because of abnormal genes, and the like.

EXAMPLES

Hereinafter, example carried out for confirming the effect of the present invention is described.

Experimental Procedure (1) Nucleic Acid Carrier

The nuclear acid carriers used in the example are listed in Table 1 shown below. In Table 1, amino acid sequence is represented using one-letter abbreviation. Also, in Table 1, "—$C_{18}$" represents the peptide of which N-terminal is modified with octadecyl group, "—Cholic A" represents the peptide in which cholic acid is linked to N-terminal via amide bond, and "Ac—" represents N-acetyl amide.

For comparing with the nucleic acid carriers listed in Table 1 (entries 1 to 21), RNAiFect™ (Qiagen), a cationic liposome-based nucleic acid carrier was used.

TABLE 1

| Entry | Amino acid sequence | SEQ ID No. |
|---|---|---|
| 1 | $(RL)_5$ | 14 |
| 2 | $(RL)_6$ | 15 |
| 3 | $(RL)_7$ | 16 |
| 4 | $(RL)_8$ | 17 |
| 5 | $(RL)_9$ | 18 |
| 6 | $(RL)_{10}$ | 19 |
| 7 | $(RL)_7$-$C_{18}$ | |
| 8 | $(RL)_7$-Cholic A | |
| 9 | $(RL)_8$-$C_{18}$ | |
| 10 | Ac-QAKKKKLDK-$(RL)_7$-GK-OH | 20 |
| 11 | Ac-SPQPKKKP-$(RL)_7$-GK-OH | 21 |
| 12 | Ac-RQARRNRRRRWR-$(RL)_7$-GK-OH | 22 |
| 13 | Ac-GPKKKRKV-$(RL)_7$-GK-OH | 23 |
| 14 | Ac-NSAAFEDLRVLS-$(RL)_7$-GK-OH | 24 |
| 15 | Ac-GRKKRRQRRRPPQG-$(RL)_7$-GK-OH | 25 |
| 16 | Ac-LPPLERLTL-GGGG-$(RL)_7$-GK-OH | 26 |
| 17 | Ac-ALQKKLEELELDE-GGGG-$(RL)_7$-GK-OH | 27 |
| 18 | Ac-LALKLAGLDI-GGGG-$(RL)_7$-GK-OH | 28 |
| 19 | Ac-SLEGAVSELSLRD-GGGG-$(RL)_7$-GK-OH | 29 |
| 20 | Ac-LPVLENLTL-GGGG-$(RL)_7$-GK-OH | 30 |
| 21 | Ac-LASLMNLGMS-GGGG-$(RL)_7$-GK-OH | 31 |

(2) Target Cells

Jurkat cell, an acute lymphoblastic leukemia, K562 cell, a chronic myelogenous leukemia and Hela cell, a uterine cervical cancer were used as the target cells.

(3) Double-Stranded Nucleic Acid Molecule

To Jurkat cell and Hela cell, siRNA (21 base pairs) against hTERT gene (human telomerase reverse transcriptase: involves in immortalization of cancer cells) was used as the double-stranded nucleic acid molecule. The base sequences of the siRNA against hTERT of Jurkat cell and Hela cell are shown in SEQ ID Nos. 32 and 33 below, respectively.

[SEQ ID No. 32]
5'-GGAGCAAGUUGCAAAGCAUTT-3'

[SEQ ID No. 33]
5'-AUGCUUUGCAACUUGCUCCTT-3'

To K562 cell, siRNA against Bcr/abl (The gene responsible for chronic myelogenous leukemia existing in Philadelphia gene, a chimeric gene form by fusion of abl gene found on chromosome 9 and bcr gene found on chromosome 22 that upregulates mitogenic signal abnormally, which result in deregulated proliferation of leukocyte cells) (21 base pairs) was used as the double-stranded nucleic acid molecule. The base sequences of the siRNA used are shown in SEQ ID Nos. 34 and 35 below.

5'-GCAGAGUUCAAAAGCCCUUTT-3' [SEQ ID No. 34]

5'-AACGGCUUUUGAACUCUGCTT-3' [SEQ ID No. 35]

(4) Preparation of Nucleic Acid Complex

A 10 μL of 200 μM aqueous solution of the peptide (in ultra-pure water) and a 10 μL of 20 μM aqueous solution of the siRNA (in ultra-pure water) were mixed at room temperature and incubated at 37° C. for 30 minutes.

(5) Transaction to Target Cell

The nucleic acid complex prepared in (4) mentioned above was added to a culture solution or a culture media of the target cell. Amount of addition was 100 nM, 200 nM or 400 nM. After adding the nuclear acid complex, incubation was conducted at 37° C. for predetermined time. Incubation time was 24 hours for Jurkat cell and K562 cell, and 48 hours for Hela cell.

(6) Evaluation of Transfection Efficiency of Nucleic Acid Complex to Target Cell Transfection efficiency of the nucleic acid complex to the target cell was evaluated using the fluorescent microscopic observation of the target cell after incubating with the nucleic acid complex prepared using fluorescently labeled double-stranded nucleic acid molecule.

(7) Evaluation of Half-Life

Half-life of the nucleic acid complex was evaluated from a time course of a decomposition rate of the siRNA of the nucleic acid complex in 10% FBS at 37° C. The decomposition rate of the siRNA was determined by formaldehyde-modified agarose gel electrophoresis of the siRNA isolated after heating the nucleic acid complex.

(8) Evaluation of Cytotoxicity

The cytotoxicity of the nucleic acid carrier was evaluated from a time course of a viability of the target cell incubated with the nucleic acid carrier.

(9) Evaluation of Silencing Effect of the Target Gene via RNAi

Evaluation of silencing effect of the target gene via RNAi was evaluated by lysing the incubated cell, amplifying the target gene using RT-PCR method and quantifying the change of the expression level of the target gene using β-actin gene as an internal standard.

Results (1) Conformation of Nucleic Acid Carrier in Nucleic Acid Complex

Circular dichromic (CD) spectra of siRNA used for the preparation of the nucleic acid complex, nucleic acid carrier 3 (number of entry shown in Table 1. The same shall apply hereinafter) consisting of amino acid sequence of $(RL)_7$ and nucleic acid complex obtained from them are shown in FIG. 1. The CD spectrum attributed to a random coil structure for the nucleic acid carrier 3 alone, whereas the CD spectrum of the nucleic acid complex showed strong Cotton effect, at 217 nm, which was a characteristic of the β-sheet structure. These results showed that the nucleic acid carrier 3 formed a β-sheet structure in which a side chain of a positively charged arginine (R) was disposed on one surface side and a side chain of a hydrophobic leucine (L) was disposed on the opposite surface side in the presence of a double-stranded nucleic acid molecule having a double helix structure. The results that either the formation of the complex with the double-stranded nucleic acid molecule or the formation of β-sheet structure were not observed for the peptide with an different amino acid sequence suggests that strong binding between both of them formed through either one or both of the electrostatic interaction between the guanidyl group of arginine and phosphate groups and hydrogen bonds between the double stranded-nucleic acid molecule and the peptide chain of the nucleic acid carrier 3.

(2) Transfection Efficiency of Nucleic Acid Complex to Target Cell

Figure 2:
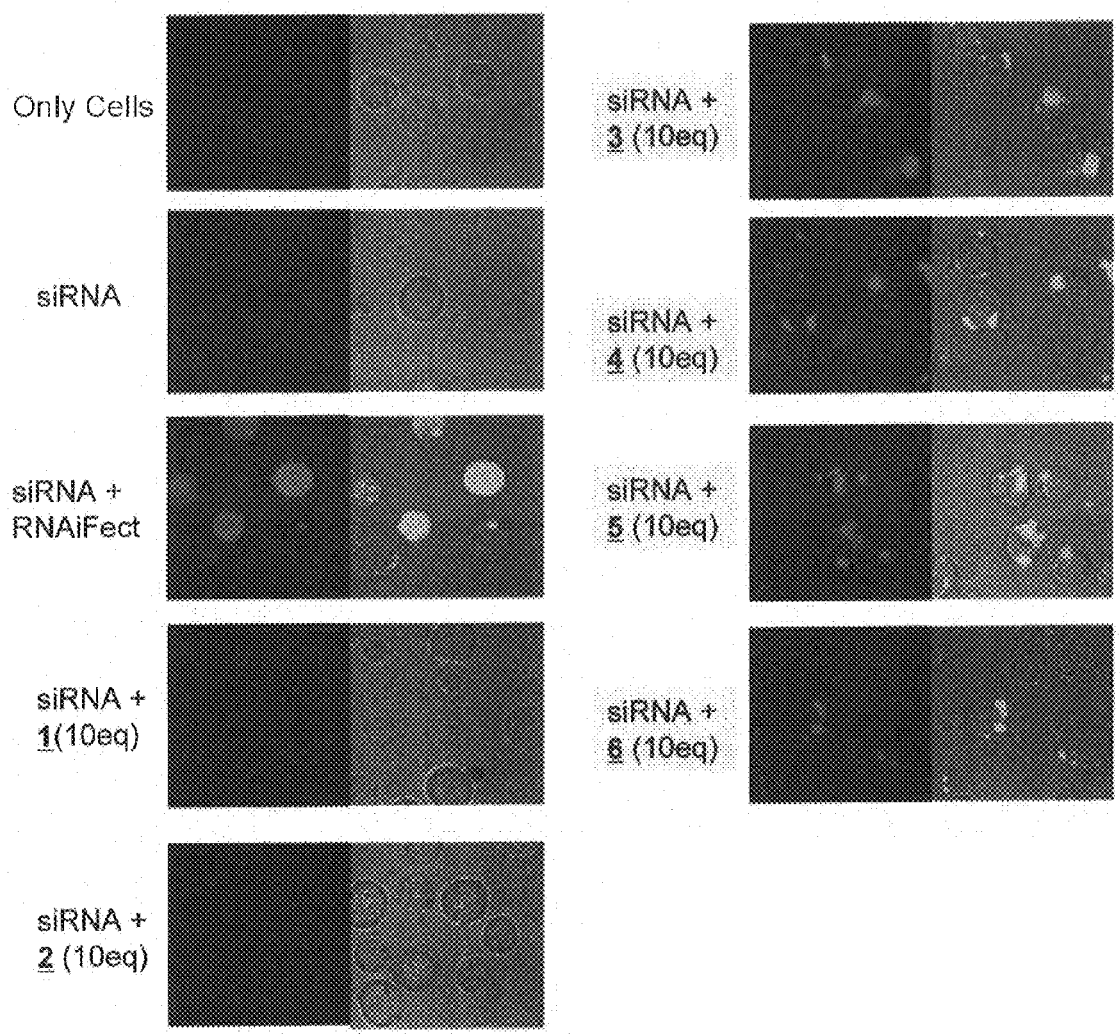
FIG. 2 shows fluorescence microscopic images showing the effect of the length of peptide chain in the nucleic acid carrier on the transfection efficiency of the nucleic acid complex into Jurkat cells.

The results of the evaluation of the transfection efficiencies of the fluorescently labeled siRNA against the hTERT to Jurkat cell obtained by using the nucleic acid carriers 1 to 6 consisting the peptides having the amino acid sequence of alternating arginine, a basic amino acid and leucine, a hydrophobic amino acid $(RL)_n$ (5≤n≤10) are shown in FIG. 2. For comparison, the result obtained by using RNAiFect is also shown. From these results, it was shown that siRNA alone cannot be transfected in cell, however, siRNA can be transfected in the cell using the nucleic acid carriers to 3 to 6 with n of 7 or more.

Figure 3:
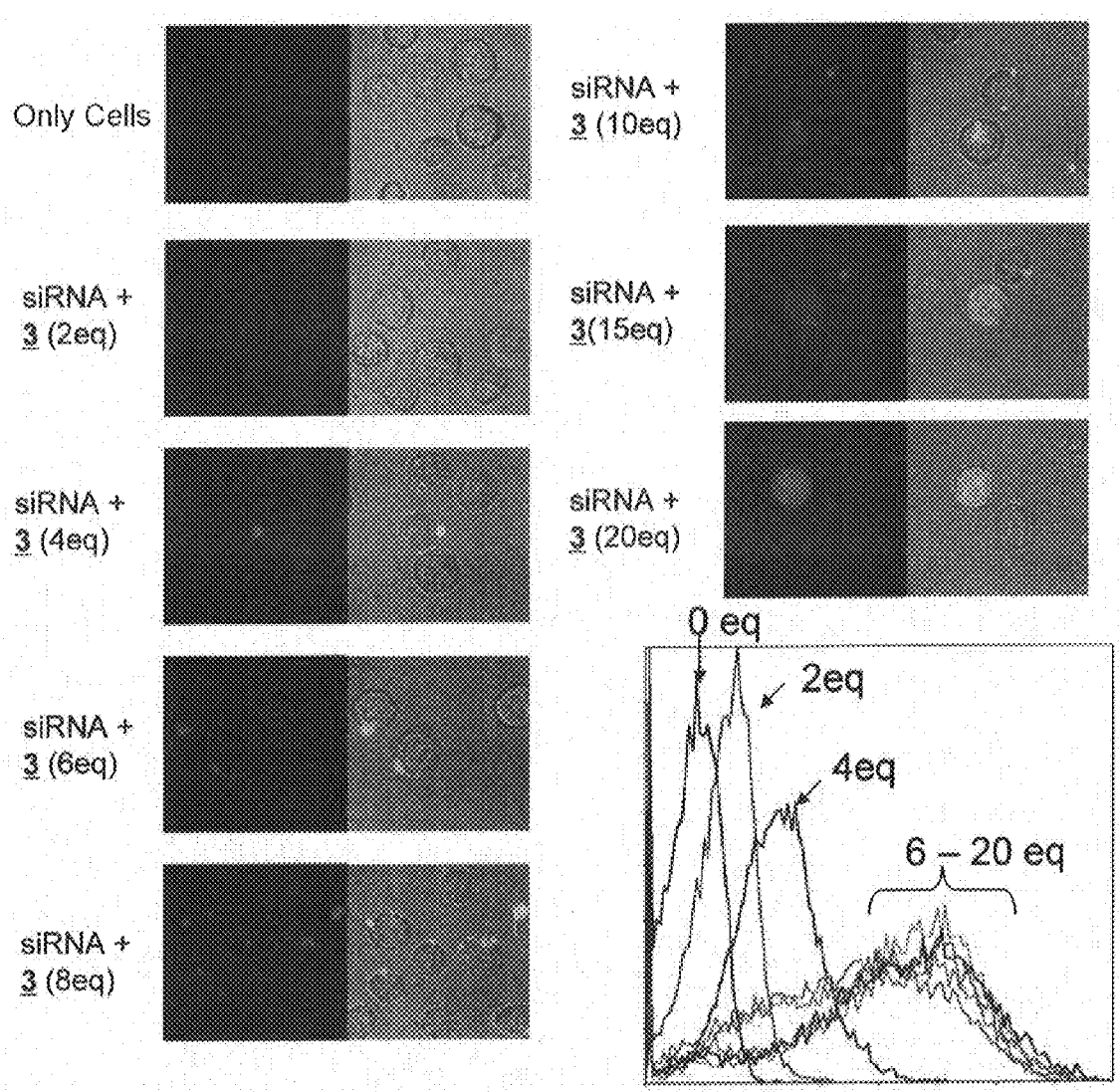
FIG. 3 shows fluorescence microscopic images and fluorescent spectra showing the effect of the molar ratio of the nucleic acid carrier on the transfection efficiency of the nucleic acid complex into Jurkat cells.

Using the nucleic acid carrier 3 having the amino acid sequence of $(RL)_7$, the effect of the molar ratio of the nucleic acid carrier 3 on the transfection efficiency of the nucleic acid complex into Jurkat cells was also evaluated. The results are shown in FIG. 3. From these results, it is shown that the molar ratio of the nucleic acid carrier 3 to siRNA is required to be 1:6 or more, more preferably 1:10 or more to sure sufficient transfection efficiency of siRNA to Jurkat cell.

Figure 4:
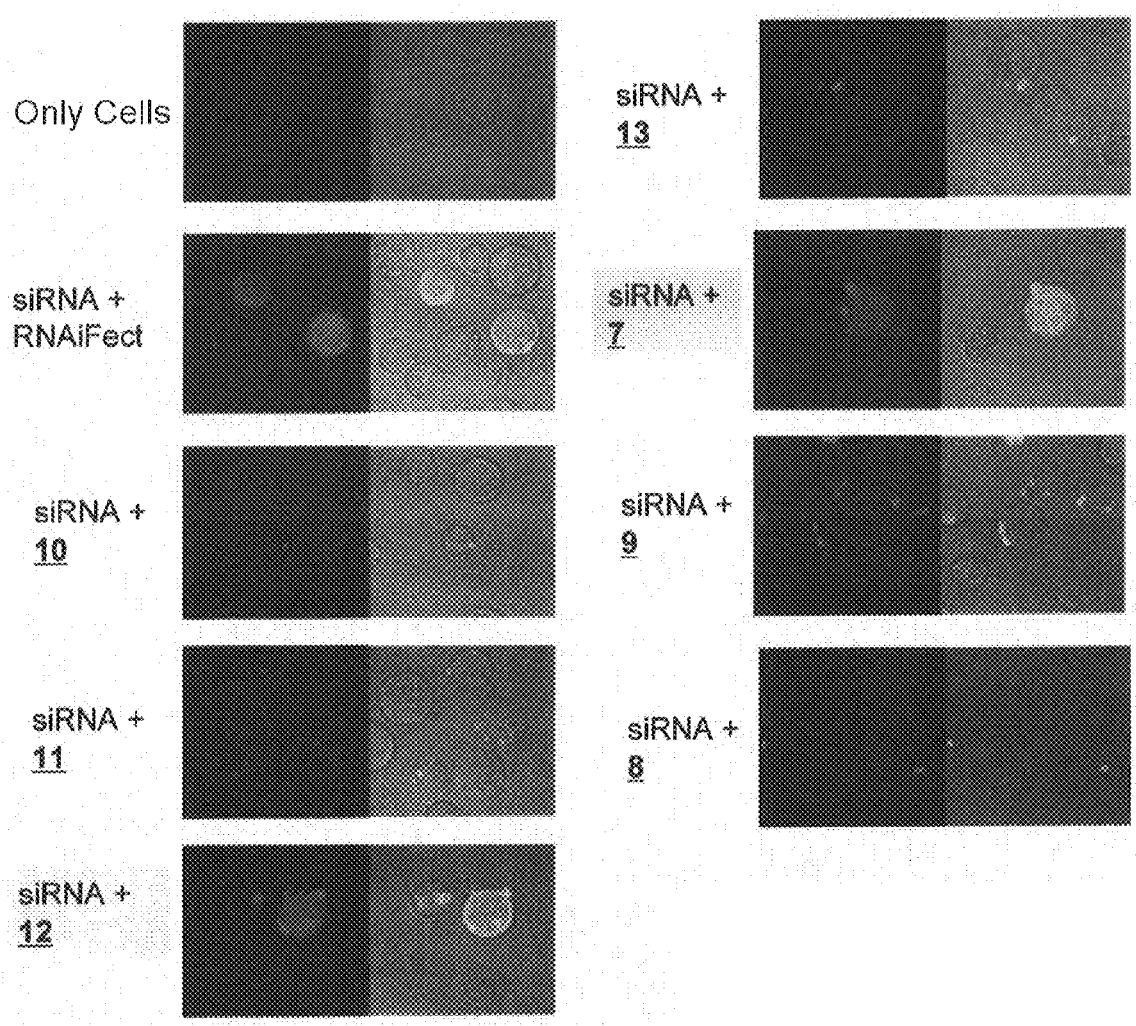
FIG. 4 shows fluorescence microscopic images showing the effect of the conjugation of nuclear localization signal (NLS) peptide and long chain carboxylic acid to (RL)$_7$ on the transfection efficiency of the nucleic acid complex into Jurkat cells.

The effect of introduction of hydrophobic group or signal peptide (NLS) on the transfection efficiency of siRNA to Jurkat cell is shown in FIG. 4. From these results, it is shown that the introduction of octadecyl group or NLS from HIV-1 Rev protein to N-terminal of the peptide significantly improves the transfection efficiency of siRNA to Jurkat cell in the combination of the nucleic acid carrier 3 and Jurkat cell (the nucleic acid carrier 12).

Figure 5:
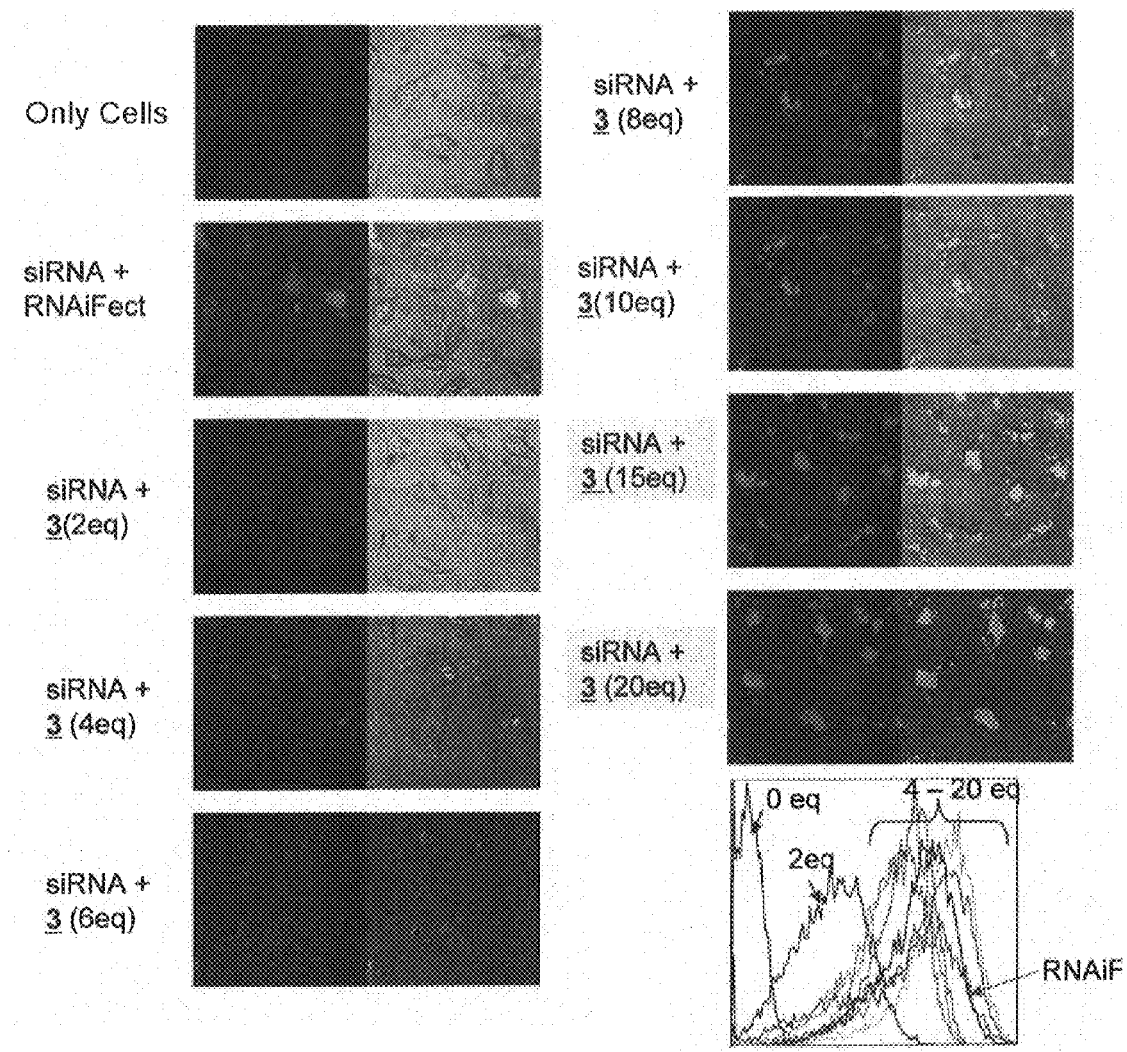
FIG. 5 shows fluorescence microscopic images and fluorescent spectra showing the effect of the molar ratio of the nucleic acid carrier on the transfection efficiency of the nucleic acid complex into HeLa cells.
Figure 6:
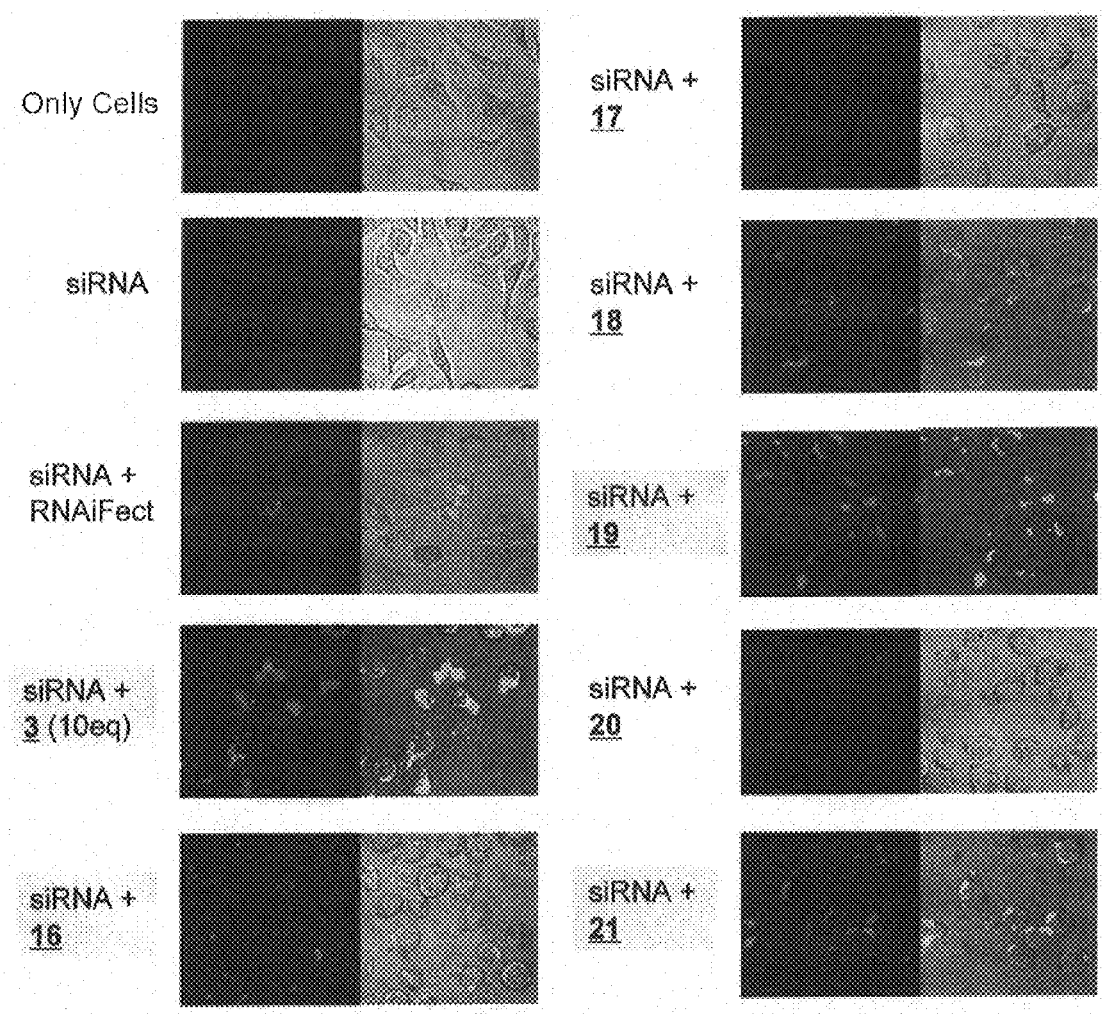
FIG. 6 shows fluorescence microscopic images showing the effect of the conjugation of nuclear export signal (NES) peptide to (RL)$_7$ on the transfection efficiency of the nucleic acid complex into HeLa cells.

The results of the similar experiments conducted using Hela cell are shown in FIGS. 5 and 6. From the results shown in FIG. 5, it is shown that the molar ratio of the nucleic acid carrier 3 to siRNA is required to be 1:15 or more to sure sufficient transfection efficiency of siRNA to Hela cell. From the results shown in FIG. 6, it is shown that the introduction of NES sequence from HIV-1 Rev protein (the nucleic acid carrier 16), NES sequence from Dsk-1 (the nucleic acid carrier 19) and NES sequence from Mstrin3 (the nucleic acid carrier 21) to the nucleic acid carrier 3 significantly improves the transfection efficiency of siRNA to Hela cell.

(3) Half-Life of siRNA in Nucleic Acid Complex

Figure 7:
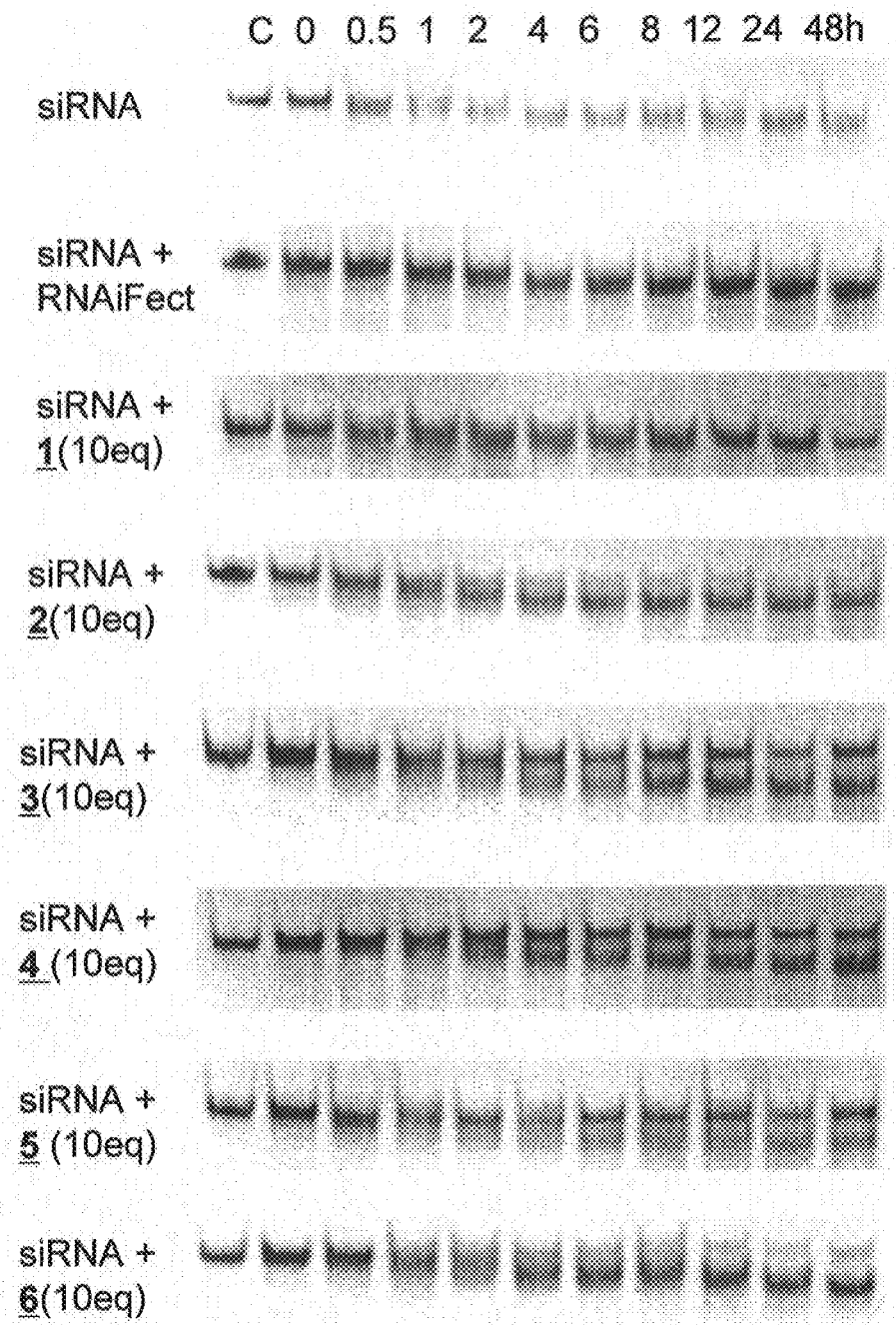
FIG. 7 shows the result of gel electrophoresis showing the time course of siRNA in the nucleic acid complex in 10% fetal bovine serum (FBS).
Figure 8:
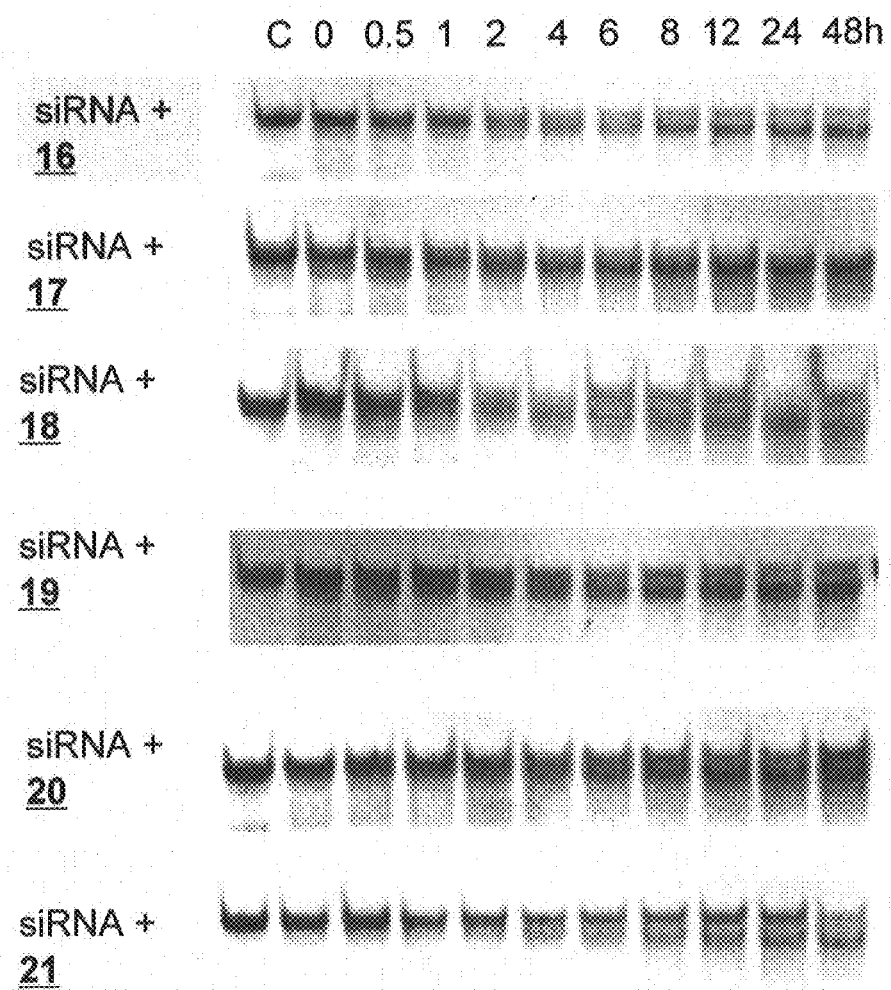
FIG. 8 shows the result of gel electrophoresis showing the time course of siRNA in the nucleic acid complex in 10% fetal bovine serum (FBS).

The results of the time course of decomposition rate of siRNA alone and siRNA in the nucleic acid complex in 10% FBS monitored using gel electrophoresis are shown in FIGS. 7 and 8, Tables 2 and 3 shown below. From the result shown in FIG. 7, it is shown that siRNA rapidly decomposes in 10% FBS (half-life of about 2 hours), however, the half life is increased to several to twenty times upon forming the nucleic acid complex with the nucleic acid carrier 3. For the nucleic carriers 1 and 2 which shows no improvement in the translation efficiency of siRNA to cell, no significant increasing of the half-life of siRNA was observed. Therefore, increased half life in 10% FBS is considered to be attributable to the formation of the nucleic acid complex. No significant increasing in the half-life due to the formation of the complex for RNAiFect. As shown in FIG. 8, increasing in the half-life were also observed for the nucleic acid carriers 16 to 21 introduced the NES sequences and significant increasing was observed for the nucleic acid carrier 16.

TABLE 2

| Sample | Half-life $t_{1/2}$ (h) |
| --- | --- |
| siRNA | 2.5 h |
| siRNA + RNAiFect | 1 h |
| siRNA + 1 | 1.8 h |
| siRNA + 2 | 1 h |
| siRNA + 3 | >>48 h |
| siRNA + 4 | 32 h |
| siRNA + 5 | 9.5 h |
| siRNA + 6 | 7 h |

TABLE 3

| Sample | Half-life $t_{1/2}$ (h) |
| --- | --- |
| siRNA + 16 | >48 h |
| siRNA + 17 | 5 h |
| siRNA + 18 | 5 h |
| siRNA + 19 | 13 h |
| siRNA + 20 | 13 h |
| siRNA + 21 | 37 h |

(4) Cytotoxicity

Figure 9:
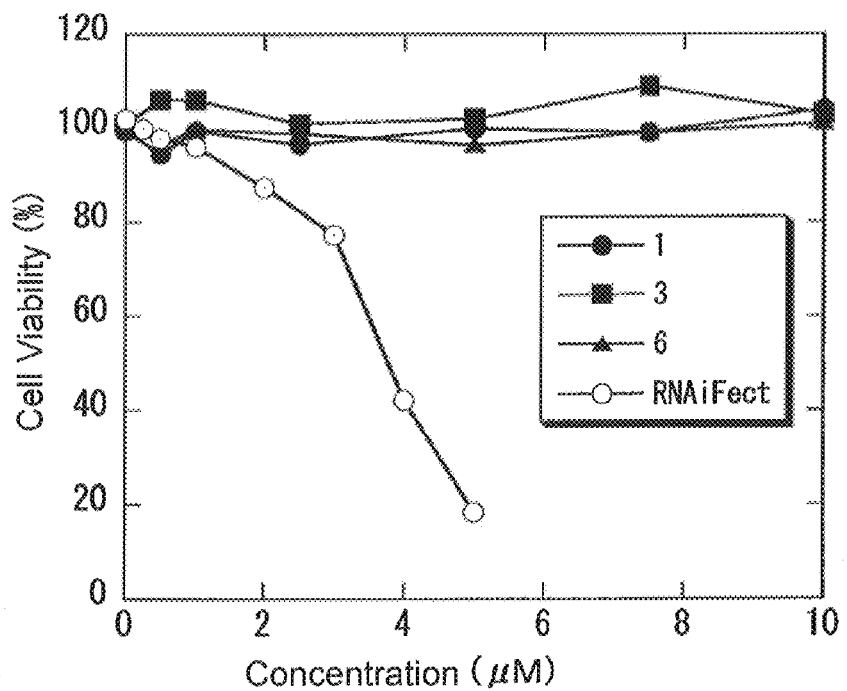
FIG. 9 shows the graph showing the time course of viability of Jurkat cell incubated in the presence of the nucleic acid carrier and RNAiFect.
Figure 10:
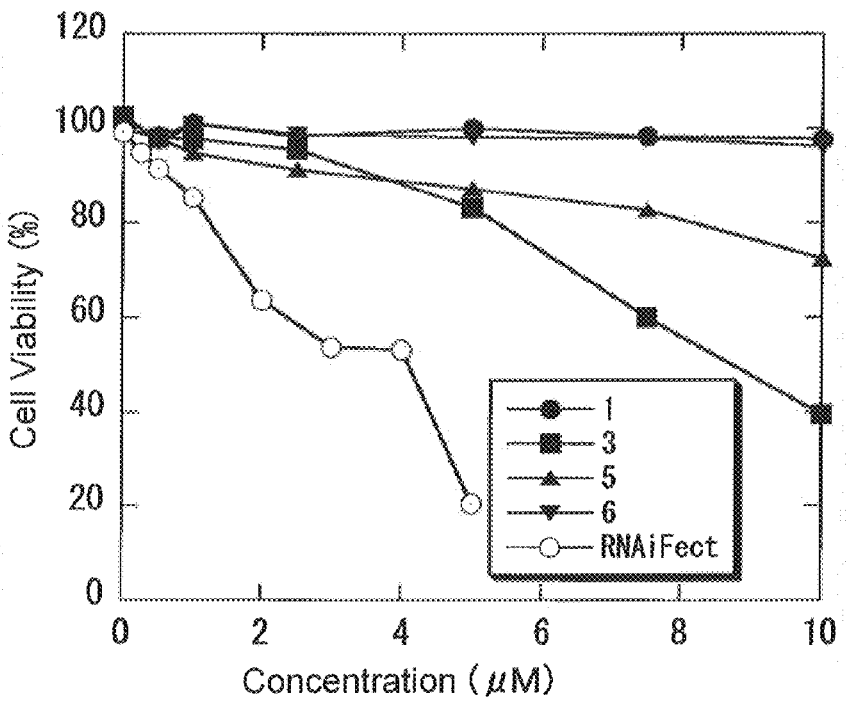
FIG. 10 shows the graph showing the time course of viability of K562 cell incubated in the presence of the nucleic acid carrier and RNAiFect.

The time course of viability of Jurkat cell and K562 cell incubated in the presence of the nucleic acid carriers 1 to 6 and RNAiFect was evaluated. The viabilities after 24 hours are shown in FIGS. 9 and 10. As shown in FIG. 9, it was found that all of the nucleic acid carriers 1 to 6 showed no significant cytotoxicity to Jurkat cell. On the other hand, as shown in FIG. 10, decreasing in the viability of K562 cell after 24 hours was observed when high concentration of the nucleic acid carriers 2 to 5 was added. However, in the concentration of about 1 to 2 μM actually used, all of the nucleic acid carriers 1 to 6 showed the cell viabilities of 90% or more, which were much higher than those observed for RNAiFect. Particularly, it was found that the nucleic acid carriers 1 and 6 showed no significant cytotoxicity to K562 cell as well.

(5) Silencing Effect of hTERT Gene of Jurkat Cell Via RNAi Using Nucleic Acid Complex The result of the observation of the expression level of the hTERT gene of Jurkat cell incubated in the presence of the nucleic acid complex of siRNA against hTERT gene of Jurkat cell (21 base pairs, SEQ ID No. 32) and the nucleic acid carrier 3 (48 hours) is shown in Table 4 below. This result shows that the nucleic acid carrier 3 has the transfection efficiency of the nucleic acid comparable to that of RNAiFect.

TABLE 4

| | mRNA expression level (relative value/%) |
| --- | --- |
| Control | 100 |
| siRNA (200 nM) | 36 |
| siRNA (200 nM) + RNAiFect | 8 |
| siRNA (200 nM) + 3 (20 eq.) | 8 |

(6) Silencing Effect of hTERT Gene of Hela Cell Via RNAi Using Nucleic Acid Complex The result of the observation of the expression level of the hTERT gene of Hela cell incubated in the presence of the nucleic acid complex of siRNA against hTERT gene of Hela cell (21 base pairs, SEQ ID No. 33) and the nucleic acid carrier 3 (48 hours) is shown in Table 5 below. This result shows that the nucleic acid carrier 3 has the transfection efficiency of the nucleic acid comparable to that of RNAiFect in the presence of smaller amount than RNAiFect.

TABLE 5

| | mRNA expression level (relative value/%) |
| --- | --- |
| Control | 100 |
| siRNA (200 nM) + RNAiFect | 38 |
| siRNA (10 nM) + 3 (20 eq.) | 41 |
| siRNA (25 nM) + 3 (20 eq.) | 19 |
| siRNA (50 nM) + 3 (20 eq.) | 17 |
| siRNA (100 nM) + 3 (20 eq.) | 10 |
| siRNA (200 nM) + 3 (20 eq.) | 8 |

(5) Silencing Effect of Bcr/Abl Gene of K562 Cell Via RNAi Using Nucleic Acid Complex The results of the observation of the expression level of the Bcr/abl gene of K562 cell incubated in the presence of the nucleic acid complex of siRNA-rev NES (covalently-linked) conjugate (100 nM) (To 5'-terminal of siRNA having a base sequence represented by SEQ ID No. 34, N-terminal of NES sequence from HIV-1 rev protein having the amino acid sequence represented by SEQ ID No. 8 is covalently linked directly) and the nucleic acid carrier 3 or a nucleic acid carrier LRALLRALLRALLRALLRALLRAL (SEQ ID No. 36, 10 eq.) (48 hours) are shown in Table 6 below.

This result shows that transfection efficiency of nucleic acid and silencing effect of Bcr/abl gene of K562 cell may be significantly enhanced by using the nucleic acid complex prepared from signal peptide-linked siRNA

TABLE 6

| | mRNA expression level (relative value/%) |
| --- | --- |
| Control | 100 |
| siRNA (100 nM) + RNAiFect | 38 |
| siRNA-revNES (100 nM) + RNAiFect | 5.4 |
| siRNA-revNES (100 nM) + LRALLRALLRALLRALLRALLRAL (10 eq.) | 36 |
| siRNA-revNES (100 nM) + 3 (10 eq.) | 4.8 |

Sequence Lasting

The invention claimed is:

1. A method for transfecting nucleic acid into a cell comprising, forming a nucleic acid complex by contacting a double-stranded nucleic acid molecule with a nucleic acid carrier,
wherein:
the nucleic acid carrier, in the presence of a double-stranded nucleic acid molecule having a double helix structure, has a peptide chain of alternating arginine and leucine that forms a β-sheet structure in which a positively charged arginine side chain is disposed on a surface side and a leucine side chain is disposed on an opposite surface side, and
the double-stranded nucleic acid molecule and the peptide chain are bound via one or both of:
electrostatic interactions between the arginine side chains and phosphate groups of the double-stranded nucleic acid molecule, and
hydrogen bonds between the double stranded-nucleic acid molecule and the peptide chain,
and
transfecting the nucleic acid complex into the cell,
wherein the method does not comprise contacting the double-stranded nucleic acid molecule with a cationic liposome.

2. The method according to claim 1 wherein the peptide chain has an amino acid sequence represented by $(RL)_n$ or $(LR)_n$, wherein R and L represent an arginine residue and a leucine residue, respectively, and n represents an integer of 5 to 10.

3. The method according to claim 1 wherein the molar ratio of the double-stranded nucleic acid molecule and the nucleic acid carrier in the step for forming a nucleic acid complex is 1:4 to 1:30.

4. The method according to claim 1 wherein the double-stranded nucleic acid molecule is siRNA.

5. The method according to claim 1 wherein the nucleic acid complex has a target cell or target cell site localization activity.

6. The method according to claim 5 wherein the localization activity is provided for by a signal peptide bound to at least a portion of the double-stranded nucleic acid molecule or the nucleic acid carrier.

7. The method according to claim 6 wherein the signal peptide has an amino acid sequence represented by any one of the following:

| | |
|---|---|
| QAKKKKLDK | [SEQ ID NO: 1] |
| SPQPKKKP | [SEQ ID NO: 2] |
| RQARRNRRRWR | [SEQ ID NO: 3] |
| GPKKKRKV | [SEQ ID NO: 4] |
| NSAAFEDLRVLS | [SEQ ID NO: 5] |
| RQIKIWFQNRRMKWKKEN | [SEQ ID NO: 6] |
| GRKKRRQRRRPPQG | [SEQ ID NO: 7] |
| LPPLERLTL | [SEQ ID NO: 8] |
| ALQKKLEELELDE | [SEQ ID NO: 9] |
| LALKLAGLDI | [SEQ ID NO: 10] |

```
                                        [SEQ ID NO: 11]
    SLEGAVSEISLRD

[SEQ ID NO: 12]
    LPVLENLTL

[SEQ ID NO: 13]
    LASLMNLGMS.
```

8. The method according to claim 6 wherein a terminal of the signal peptide is bound to a peptide chain of the nucleic acid carrier or a terminal of the double-stranded nucleic acid.

9. A nucleic acid complex comprising:
a nucleic acid carrier and a double-stranded nucleic acid molecule,
wherein:
the nucleic acid carrier, in the presence of a double-stranded nucleic acid molecule having a double helix structure, has a peptide chain of alternating arginine and leucine that forms a β-sheet structure in which a positively charged arginine side chain is disposed on a surface side and a leucine side chain is disposed on the opposite surface side,
the double-stranded nucleic acid molecule and nucleic acid carrier are bound via one or both of:
electrostatic interactions between the side chains of arginine and phosphate groups of the double-stranded nucleic acid molecule, and
hydrogen bonds between the double stranded-nucleic acid molecule and the peptide chain that forms the β-sheet structure,
and
the nucleic acid complex does not comprise a cationic liposome.

10. The nucleic acid complex according to claim 9 wherein the peptide chain has an amino acid sequence represented by $(RL)_n$ or $(LR)_n$, wherein R and L represent an arginine residue and a leucine residue, respectively, and n represents an integer of 5 to 10.

11. The nucleic acid complex according to claim 9 wherein the double-stranded nucleic acid molecule is siRNA.

12. The nucleic acid complex according to claim 9 wherein a signal peptide having a localizing activity toward a target cell or target cell site is bound to at least a portion of the double-stranded nucleic acid molecule or the nucleic acid carrier.

13. The nucleic acid complex according to claim 12 wherein the signal peptide has an amino acid sequence represented by any one of the following:

```
                                        [SEQ ID NO: 1]
    QAKKKKLDK

[SEQ ID NO: 2]
    SPQPKKKP

[SEQ ID NO: 3]
    RQARRNRRRWR

[SEQ ID NO: 4]
    GPKKKRKV

[SEQ ID NO: 5]
    NSAAFEDLRVLS

[SEQ ID NO: 6]
    RQIKIWFQNRRMKWKKEN

[SEQ ID NO: 7]
    GRKKRRQRRRPPQG

[SEQ ID NO: 8]
    LPPLERLTL

[SEQ ID NO: 9]
    ALQKKLEELELDE

[SEQ ID NO: 10]
    LALKLAGLDI

[SEQ ID NO: 11]
    SLEGAVSEISLRD

[SEQ ID NO: 12]
    LPVLENLTL

[SEQ ID NO: 13]
    LASLMNLGMS.
```

14. The nucleic acid complex according to claim 12 wherein a terminal of the signal peptide is bound to a peptide chain of the nucleic acid carrier or a terminal of the double-stranded nucleic acid.

\* \* \* \* \*